United States Patent [19]

Sinn

[11] Patent Number: 5,351,822
[45] Date of Patent: Oct. 4, 1994

[54] RETAINER FOR AN ELONGATED SURGICAL INSTRUMENT

[75] Inventor: Hans-Jurgen F. Sinn, Fairfield, Conn.

[73] Assignee: United States Surgical Corporation, Norwalk, Conn.

[21] Appl. No.: 18,681

[22] Filed: Feb. 17, 1993

[51] Int. Cl.⁵ .................. B65D 85/08; B65D 73/00
[52] U.S. Cl. ........................ 206/363; 206/478
[58] Field of Search .............. 206/63.3, 63.5, 363, 206/364, 365, 366, 370, 419, 438, 443, 477–483, 485–489

[56] References Cited

U.S. PATENT DOCUMENTS

| | | |
|---|---|---|
| 2,133,710 | 10/1938 | Lowey .................. 206/383 |
| 2,332,412 | 10/1943 | Taylor . |
| 2,368,753 | 2/1945 | Elliott et al. ............ 206/419 |
| 2,394,457 | 2/1946 | Lobl .................... 206/380 |
| 2,399,000 | 9/1943 | Carroll . |
| 2,415,151 | 2/1947 | Taylor et al. . |
| 2,617,523 | 11/1952 | Zoller . |
| 2,692,676 | 10/1954 | Grover . |
| 2,990,059 | 6/1961 | Hitt .................... 206/365 |
| 3,037,619 | 6/1962 | Stevans . |
| 3,136,418 | 6/1964 | Stacy . |
| 3,363,751 | 1/1968 | Shave et al. . |
| 3,444,994 | 5/1969 | Kaepernik et al. . |
| 3,487,917 | 1/1970 | Shave et al. . |
| 3,568,883 | 3/1971 | Reynolds . |
| 3,939,969 | 2/1976 | Miller et al. . |
| 3,951,261 | 4/1976 | Mandel et al. . |
| 3,967,728 | 7/1976 | Gordon et al. .......... 206/438 |
| 3,985,227 | 10/1976 | Thyen et al. . |
| 4,014,434 | 3/1977 | Thyen . |
| 4,120,395 | 10/1978 | Mandel et al. . |
| 4,121,711 | 10/1978 | Bolanowski . |
| 4,135,623 | 1/1979 | Thyen . |
| 4,239,104 | 12/1980 | Roccaforte et al. . |
| 4,249,656 | 2/1981 | Cerwin et al. . |
| 4,253,563 | 3/1981 | Komarnycky . |
| 4,284,194 | 8/1983 | Flatau . |
| 4,386,697 | 6/1983 | Zocher ................. 206/383 |
| 4,406,363 | 9/1983 | Aday . |
| 4,412,613 | 11/1983 | Kubas . |
| 4,412,614 | 11/1983 | Ivanov et al. . |
| 4,413,727 | 11/1983 | Cerwin et al. . |
| 4,483,437 | 11/1984 | Cerwin et al. . |
| 4,491,218 | 1/1985 | Aday . |
| 4,496,045 | 1/1985 | Ferguson et al. . |
| 4,533,041 | 8/1985 | Aday et al. . |
| 4,555,016 | 11/1985 | Aday et al. . |
| 4,574,948 | 3/1986 | Huck et al. . |
| 4,574,957 | 3/1986 | Stead . |
| 4,615,435 | 10/1986 | Alpern et al. . |
| 4,884,681 | 12/1989 | Roshdy et al. . |
| 4,887,710 | 12/1989 | Roshdy et al. . |
| 4,896,767 | 1/1990 | Pinheiro . |
| 4,946,043 | 8/1990 | Roshdy et al. . |
| 5,127,518 | 7/1992 | Hölzwarth et al. . |
| 5,131,537 | 7/1992 | Gonzales ............... 206/364 |
| 5,226,535 | 7/1993 | Rosdhy et al. . |
| 5,234,106 | 8/1993 | Transue et al. . |

FOREIGN PATENT DOCUMENTS 1385231  11/1964  France .................. 206/476

*Primary Examiner*—Jimmy G. Foster

[57] ABSTRACT

A retainer for an elongated surgical implement, includes a middle panel and distal and proximal end panels which are foldably connected to the middle panel so as to be movable to an overlap configuration. The proximal end panel has gussets for dividing the panel into two portions, one of which contacts a surface of the middle panel and the other of which is spaced apart from the surface of the middle panel to create a cavity within which the instrument is positioned. The retainer includes tabs for locking the end panels in their overlap configuration.

22 Claims, 2 Drawing Sheets

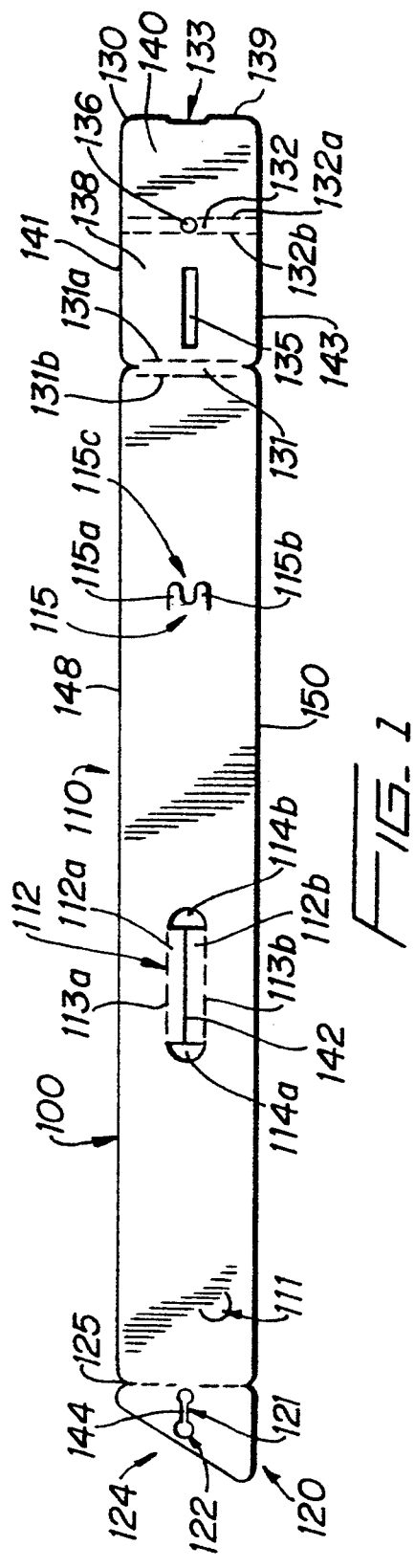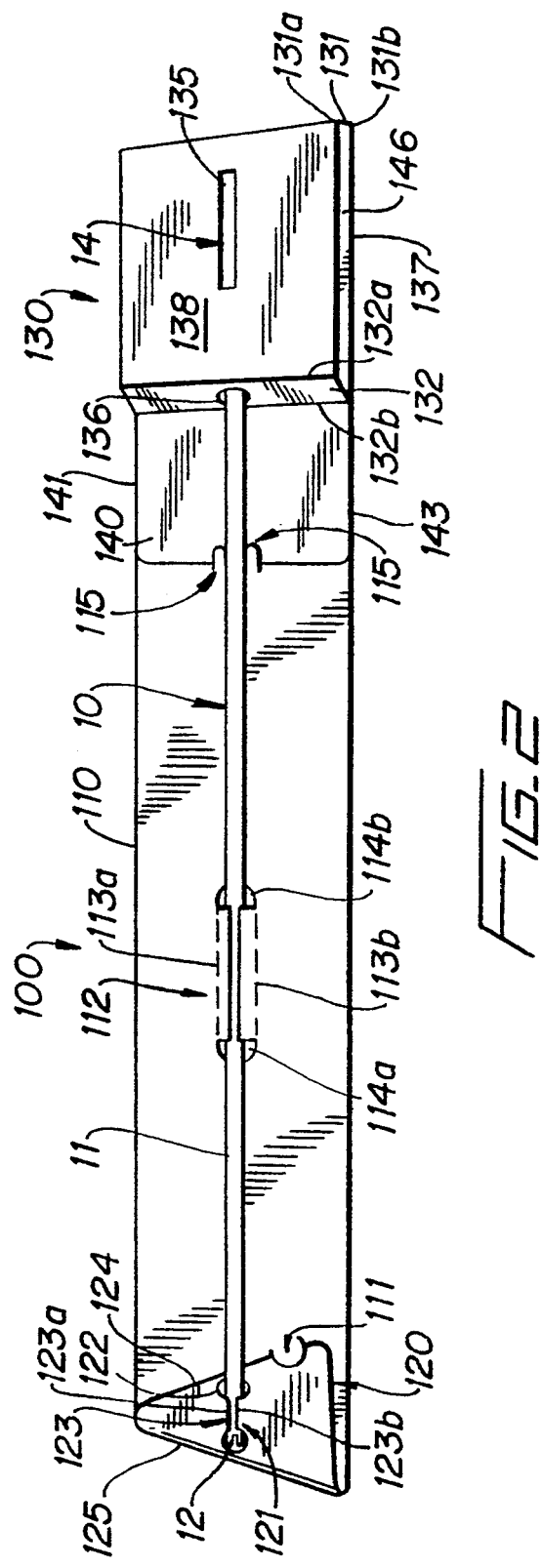

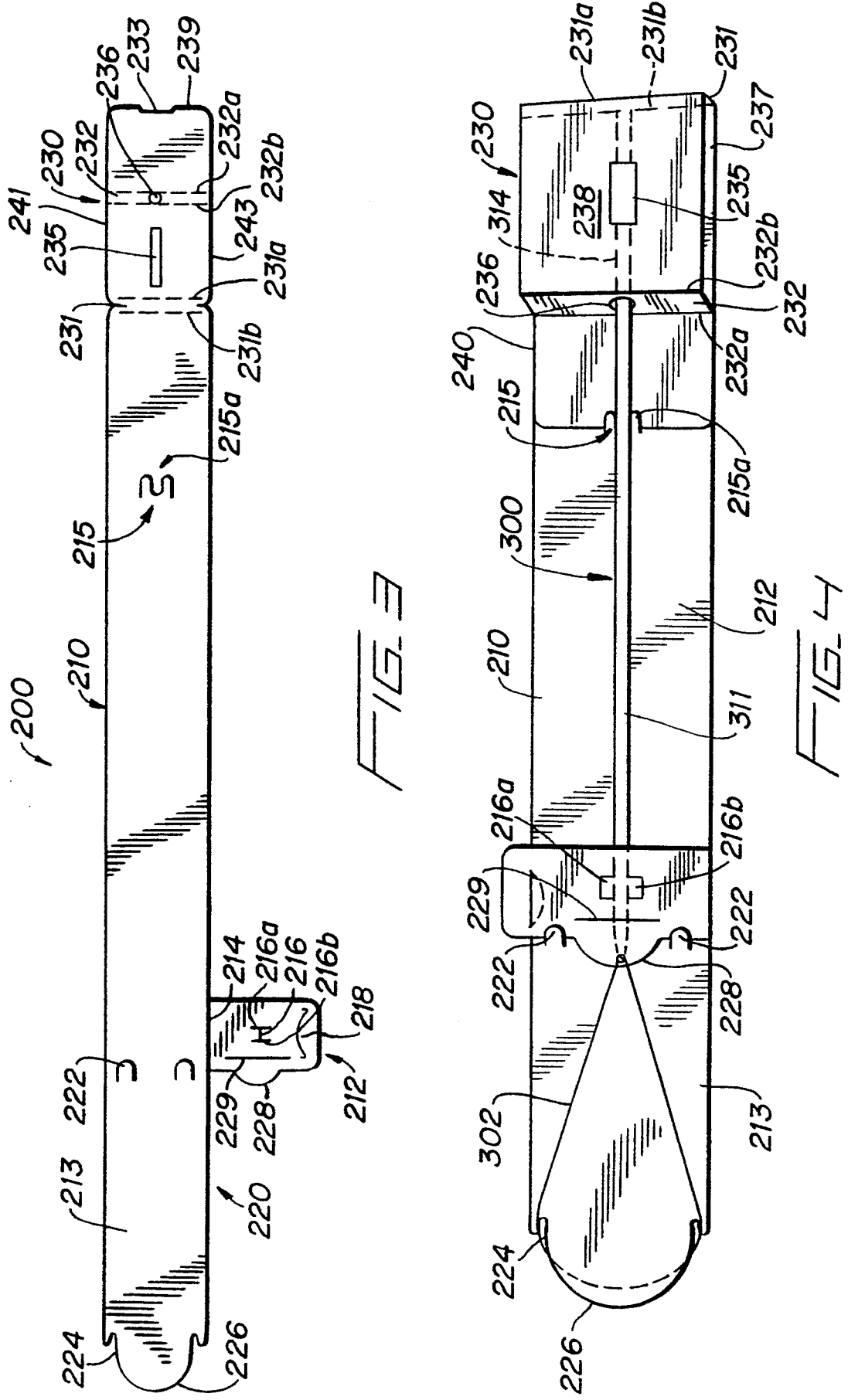

RETAINER FOR AN ELONGATED SURGICAL INSTRUMENT

BACKGROUND OF THE INVENTION

1. Field of the Invention

The present invention relates to a retainer for securely packaging and holding an elongated surgical instrument in position within a package.

2. Background of the Art

Various types of instrument retainers are known for surgical items. Retainers are commonly used to prevent damage to, and maintain sterility of, a surgical instrument during shipping and subsequent storage. Further, the retainer facilitates handling and dispensing of surgical items as needles, sutures and other surgical items.

One example of a structure for packaging an elongated surgical instruments is shown in U.S. Pat. No. 3,910,410 which discloses a plastic tray having a cavity for receiving the instrument, the tray being covered by a lid. U.S. Pat. Nos. 4,884,681 and 4,887,710, both to Roshdy et al. are examples of two prior art packages which disclose a retainer for surgical sutures. The retainer includes a suture winding panel with the panel having a pair of holding panels foldably connected to longitudinal edges of the suture winding panel.

Other suture or needle/suture retainers are exemplified in U.S. Pat. Nos. 4,572,363; 4,412,614; 4,391,365; 4,135,623; 3,444,994; and 2,692,676, as well as in other U.S. patents.

The construction of a retainer requires the combination of two seemingly opposite properties. On one hand the retainer must securely hold the surgical item to prevent damage and dislodging caused by jostling during transportation, handling and storage of the item. On the other hand, the item should be easily releasable from the retainer by the surgeon or other health care worker. A further desirable feature is that the retainer be economical to manufacture.

The present invention provides a retainer for an elongated surgical instrument which provides the above properties.

SUMMARY OF THE INVENTION

Provided herein is a retainer for releasably holding an elongated surgical instrument. The retainer comprises a middle panel which is foldably connected to a distal end panel and to a proximal end panel. The distal end panel is movable into a position wherein the distal end panel overlaps the middle portion. The proximal end panel is foldably connected to the middle panel by first and second spaced apart fold lines and movable into a position wherein a first portion of the first proximal portion of the proximal end panel overlaps the middle panel. The proximal end panel includes third and fourth spaced-apart fold lines for separating the proximal end panel into a second portion in overlapping contact with the middle panel when the proximal end panel has been moved to the overlap position. The second portion of the proximal end panel is raised from the surface of said middle panel when the proximal end panel has been moved to the overlap position. The proximal end panel also includes an aperture located in the space between said third and fourth fold lines for receiving the surgical instrument.

Further included is a first member for locking the proximal end panel in the overlap position and a second member for locking the distal panel in the overlap position. The first locking member includes a proximally oriented tab located on the middle panel, and a notch positioned on an edge of said proximal end panel for engaging the proximally oriented tab. The means for locking the distal end panel can include a tab located on said middle panel for engaging an edge of the distal end panel when the distal end panel is moved to said overlap position.

BRIEF DESCRIPTION OF THE DRAWINGS

FIG. 1 is a plan view of a retainer in accordance with the present invention shown in unfolded configuration;

FIG. 2 is a perspective view of a retainer of the present invention shown in combination with an elongated surgical instrument;

FIG. 3 is a plan view of a retainer in accordance with the present invention shown in an unfolded configuration; and FIG. 4 is a perspective view of the retainer shown in FIG. 3 and in combination with an elongated surgical instrument with a looped suture.

DETAILED DESCRIPTION OF PREFERRED EMBODIMENTS

The retainer of the present invention provides means for packaging an elongated surgical instrument in a manner which prevents damage during transportation and storage, yet is also easily removed by the user. The surgical instruments for which this retainer are specifically designed are elongated and relatively narrow so that they may be inserted through a trocar cannula for use in minimally invasive surgical procedures such as laparoscopic or endoscopic procedures.

Referring to the first embodiment of the invention shown in FIGS. 1 and 2, the retainer 100 of the first embodiment includes a middle panel 110 foldably connected to a proximal panel 130 and to a distal panel 120. The linear panels which comprise the foldable connections are weakened by perforation or scoring. Assembly of the retainer for use comprises folding the panels along the fold lines to achieve the structure substantially as shown in FIG. 2. The retainer 100 is preferably fabricated from a relatively stiff paper stock or from a sheet of polymeric material.

The proximal panel 130 receives and retains the proximal end 14 of the elongated surgical instrument. The proximal panel 130 includes an upper longitudinal edge 141, a lower longitudinal edge 143 and a first gusset 131 which is a transverse edge or fold line 132b which also connects the proximal panel 130 to the middle panel 110. The first gusset 131 is defined by spaced apart and perforated fold lines 131a and 131b. The proximal end panel 130 includes a second gusset 132 defined by spaced apart and perforated fold lines 132a and 132b. The proximal end panel 130 is formed by an upper portion 138 and an overlapping portion 140 which are foldably connected by perforated fold lines 132a and 132b of second gusset 132. A proximal instrument engaging aperture 136 is positioned at or near the center of the second gusset 132. The proximal end panel 130 is adapted to bend at second gusset 131 so as to fold over middle panel 110. A notch 133 is located at the proximal edge 139 and is adapted to engage and fit under pronged tab 115 so as to lock proximal end panel 130 in position, thereby causing a slight uplifting of tab 115. The second gusset 132 serves to divide proximal end panel 130 into an upper portion 138 and a lower portion 137 through which the instrument is positioned. A window 135 is located in the upper portion 138 to permit viewing of the proximal end of the instrument, particularly imprinted product or manufacturing information.

Middle panel 110 is an elongated substantially rectangular panel member having a distal tab 111, a central shaft holding fixture 112, and a pronged tab 115. The middle panel 110 includes an upper longitudinal edge 148, a lower longitudinal edge 150 and transverse edges or fold lines 125 and 131 which foldably connect the middle panel 110 to the distal end panel 120 and the proximal end panel 130, respectively. The distal tab 111 retains the distal edge 124 and a portion of distal end panel 120 when the distal end panel 120 is folded over into engagement with the middle panel 110. Proximal tab 115 has proximally pointing spaced apart prongs 115a and 115b which define a central groove 115c for cradling the shaft of an elongated instrument 10. When the retainer is constructed the tab 115 and uplifted by the engagement of overlapping portion 140 under tab 115 which centers and retains the shaft 11 of the instrument 10. The middle panel 110 also includes shaft holding fixture 112 having distal and proximal openings 114a and 114b, respectively, and perforated fold lines 113a and 113b. Together with longitudinal slit 142, fold lines 113a and 113b define flaps 112a and 112b which serve to retain the elongated shaft 11 of the instrument adjacent the middle panel 110.

As shown in FIG. 2, the length of the distal end panel 120 is greater than the length from first gusset 131 to the base of the tab 115. The amount by which the length of the distal end panel exceeds the length from the first gusset 131 to the base of the tab 115 is substantially equal to the width of the first gusset 131 and second gusset 132

The distal end panel 120 is foldably connected by fold line 125 to the middle panel 110. The distal panel 120 includes instrument engaging aperture 121 for engaging the distal end portion of the instrument, such as knot pusher 10, as illustrated in FIG. 2. The aperture 121 includes instrument receiving aperture 122 and a slit 144 which forms flaps 123a and 123b. The flaps 123 are disposed over the distal end 12 of the instrument 10 when the instrument is engaged therein. The distal edge 124 of distal end panel 120 is angled for enhanced construction and oriented non-perpendicularly to the lengthwise orientation of the retainer 100. The distal end panel 120 can be substantially triangular in shape with distal edge 124 constituting the hypotenuse of that triangle. The distal end is adapted to bend at fold line 125, which is a linear portion of the retainer 100 which has been weakened by perforation or scoring. When the retainer 100 is constructed the distal end panel 120 is folded to overlap middle panel 110, and the distal edge 124 is inserted under and held down by tab 111.

When fully engaged in the constructed retainer 100, the proximal portion 13 of the instrument 10 is inserted in and retained within aperture 136. The instrument shaft 11 is retained by the center of tab 115 which, when slightly raised by its engagement of the notch 133 of its proximal edge 139, cradles the instrument shaft 11 to inhibit lateral movement thereof. The shaft portion 11 of the instrument extends through the fixture 112 where the shaft 11 is disposed through apertures 114a and 114b and held down by flaps 112a and 112b which overlap the instrument shaft 11. The distal forked end 12 of the instrument 10 extends through aperture 122 and is secured by flaps 123.

The retainer 100 is constructed by taking overlapping panel 140 and inserting the notch 133 formed along the proximal edge 139 of the overlapping panel 140 under the tab 115 thereby forming a raised tab. In this process a cavity 146 is formed between upper portion 138 and lower portion 137. The proximal end 13 of surgical instrument 10 is inserted through distal opening 114a, under flaps 113a and 113b, through proximal opening 114b, through central groove 115c and through aperture 136. The proximal end 13, and particularly any printed indicia thereon, may be viewed through window 135. The distal end 12 of the surgical instrument 10 is retained on the retainer by folding distal end panel 120 along its fold line 125 such that the distal edge 124 is engaged under the distal tab 111. While the proximal end 14 of the instrument 10 is retained in the proximal end panel 130, the shaft 11 is retained in the central groove 115c and by the shaft holding fixture 112 of the middle panel 110. The distal end 12 of the instrument 10 is retained by the distal end panel 120, specifically the flaps 123.

The surgical instrument 10 is removed from the retainer 100 by removing the distal end panel 120 from its engagement with the tab 111. The instrument shaft 11 of the instrument 10 is then removed from its engagement under the flaps 113a and 113b by pulling the shaft 11 upward through the slit 142. The proximal end 14 of the instrument 10 is then moved distally, in the direction of distal end panel 120, and removed from the engaging aperture 136.

A second embodiment of the invention is shown in FIGS. 3 and 4 and identified as retainer 200. Similar in many respects to the first embodiment the retainer 210 includes a middle panel 210 foldably connected to a proximal panel 230 and a distal panel 220. The linear panels which comprise the foldable connections are weakened by perforations or scoring. The retainer 200 is assembled by folding the panels along the fold lines to achieve the retainer shown retaining an endoscopic suture ligating loop 300 in FIG. 4. The retainer 200 is preferably fabricated from a relatively stiff paper stock or from a sheet of polymeric material.

The proximal end panel 230 receives and retains the proximal end 314 of the elongated surgical instrument 300. The proximal end panel 230 includes an upper longitudinal edge 241, a lower longitudinal edge 243, and first gusset 232 formed by spaced apart and perforated fold lines 232a and 232b. An instrument receiving aperture 236 is positioned at or near the center of the first gusset 232. Proximal end panel 230 further includes a second gusset 231 defined by spaced apart and perforated fold lines 231a and 231b. The proximal end panel 230 is adapted to bend at second gusset 231 so as to fold over middle panel 210. A notch 233 is located at the proximal edge 239 and is adapted to engage and fit under pronged tab 215 which locks proximal end panel 230 in position. The engagement of the notch 233 in tab 215 causes a slight uplifting of tab 215. When the retainer is constructed, the first gusset 232 serves to divide proximal end panel 230 into an upper portion 238 and a lower portion 237 through which the instrument is positioned. A window 235 is located in the upper portion 238 to permit viewing of printed indicia on the proximal end of the instrument.

Middle panel 210 is an elongated strip which includes shaft retaining panel 212 and the pronged tab 215. The middle panel 210 is connected to the proximal panel 230 and the distal panel 220.

The distal panel 220 includes retaining panel 212 and loop panel 213. When the retainer 200 is constructed, the retaining panel 212 folds over to overlap the middle panel 210 and retain the instrument against the retainer 200. The retaining panel 212 has a flap 216 which includes foldable flaps 216a and 216b which position the instrument shaft 311 along the middle panel 210 when the retaining panel is folded over the middle panel 210. A flap 218, which is stamped or cutout of the retaining panel 212, engages over the edge 215 of the retainer to position the retaining panel 212 over the retainer 200. A tab 228 and slot 229 are also included on retaining panel 212 for further stabilizing and retaining the instrument in the retainer. The slot 229 allows for flexibility of the retaining panel 212 when it is in its folded over position while the tab 228 restrains movement of the instrument which is distal to the retaining panel.

The loop panel 213 of distal panel 220 includes channels 224 for retaining, in this embodiment, the wire loop 302 of the instrument in position on the retainer 300. The distal arc portion 226 supports and protects the wire loop 302 against damage and bending.

Referring to FIG. 4, the instrument 300 is shown retained in the constructed retainer 200. The proximal portion 314 of the instrument 300 is inserted in and retained within aperture 236. The instrument shaft 311 is retained by the center of tab 215 which, when slightly raised by its engagement of the proximal edge notch 233 cradles the instrument shaft 311 to inhibit lateral movement thereof. The shaft portion 311 of the instrument extends through the flaps 216a, 216b and is retained under retaining panel 212 which overlaps the instrument shaft 311. The wire loop end 302 of the instrument 310 is retained by channels 224 at the distal end of the retainer 200.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A retainer for releasably holding an elongated surgical instrument having a distal end and a proximal end, which comprises:
   a) a middle panel;
   b) a distal end panel foldably connected to said middle panel and movable into a position wherein said distal end panel overlaps said middle panel;
   c) a proximal end panel foldably connected to said middle panel by first and second spaced apart fold lines and movable into a position wherein said proximal end panel overlaps said middle panel, said proximal end panel having third and fourth spaced-apart fold lines for separating said proximal end panel into a first portion which contacts a surface of said middle panel when said proximal end panel has been moved to said overlap position, and a second portion which is spaced-apart from said surface of said middle panel when said proximal end panel has been moved to said overlap position;
   d) means for locking said proximal end panel in said overlap position, said proximal end panel locking means including a proximally oriented tab located on the middle panel; and,
   e) means for locking said distal end panel in said overlap position.

2. The retainer of claim 1, wherein said proximal end panel includes an aperture located in the space between said third and fourth fold lines for receiving the surgical instrument.

3. The retainer of claim 1, wherein said means for locking said proximal panel further includes a notch positioned on an edge of said proximal end panel for engaging said proximally oriented tab.

4. The retainer of claim 3 wherein said proximally oriented tab includes two proximally pointing prongs defining a space therebetween for receiving the surgical instrument.

5. The retainer of claim 1, wherein said means for locking said distal end panel includes a tab located on said middle panel for engaging an edge of the distal end panel when said distal end panel is moved to said overlap position.

6. The retainer of claim 1, wherein said middle panel includes flap means for releasably holding said surgical instrument.

7. The retainer of claim 1, wherein said distal end panel includes an aperture for receiving the distal end portion of said surgical instrument.

8. The retainer of claim 1, wherein said distal end panel is foldably connected to said middle panel along a longitudinal edge of said middle panel.

9. The retainer of claim 8, wherein said distal end panel includes a first flap for engaging said distal end panel over said middle panel and a pair of second flaps for prohibiting lateral movement of the instrument.

10. The retainer of claim 9, said distal end panel further comprising a distal edge which is semicircular shaped and includes a pair of oppositely positioned channels for receiving and engaging the distal end of the elongated surgical instrument.

11. The retainer of claim 1, wherein said retainer is fabricated from a material selected from the group consisting of paper and polymeric material.

12. In combination:
   a) an elongated surgical instrument having a distal end and a proximal end; and
   b) a retainer for releasably holding said elongated surgical instrument, said retainer including,
      i) a middle panel,
      ii) a distal end panel foldably connected to said middle panel and movable into a position wherein said distal end panel overlaps said middle panel,
      iii) a proximal end panel foldably connected to said middle panel by first and second spaced apart fold lines and movable into a position wherein said proximal end panel overlaps said middle panel, said proximal end panel having third and fourth spaced-apart fold lines for separating said proximal end panel into a first portion which contacts a surface of said middle panel when said proximal end panel has been moved to said overlap position, and a second portion which is spaced-apart from said surface of said middle panel when said proximal end panel has been moved to said overlap position,
      iv) means for locking said proximal end panel in said overlap position, said proximal end panel locking means including a proximally oriented tab located on the middle panel; and, v) means for locking said distal end panel in said overlap position.

13. The combination of claim 12, wherein said proximal end panel includes an aperture located in the space between said third and fourth fold lines for receiving the surgical instrument.

14. The combination of claim 12, wherein said means for locking said proximal panel further includes a notch positioned on an edge of said proximal end panel for engaging said proximally oriented tab.

15. The combination of claim 12, wherein said proximally oriented tab includes two proximally pointing prongs defining a space therebetween for receiving the surgical instrument.

16. The combination of claim 12, wherein said means for locking said distal end panel includes a tab located on said distal end panel for engaging an edge of the middle panel when said distal end panel is moved to said overlap position.

17. The combination of claim 12, wherein said middle panel includes flap means for releasably holding said surgical instrument.

18. The combination of claim 12, wherein said distal end panel includes an aperture for receiving the distal end portion of said surgical instrument.

19. The combination of claim 12, wherein said distal end panel includes a semi-circular shaped distal end having a pair of oppositely positioned channels for retaining said surgical instrument.

20. The combination of claim 12, wherein said retainer is fabricated from a material selected from the group consisting of paper and polymeric material.

21. The combination of claim 12, wherein said surgical instrument is configured and dimensioned to fit through a cannula for use in minimally invasive surgical procedures.

22. A retainer for releasably holding an elongated surgical instrument having a distal end and a proximal end, which comprises:
   a) a middle panel;
   b) a distal end panel foldably connected to said middle panel and movable into a position wherein said distal end panel overlaps said middle panel;
   c) a proximal end panel foldably connected to said middle panel by first and second spaced apart fold lines and movable into a position wherein said proximal end panel overlaps said middle panel,
   said proximal end panel having third and fourth spaced-apart fold lines for separating said proximal end panel into a first portion which contacts a surface of said middle panel when said proximal end panel has been moved to said overlap position, and a second portion which is spaced-apart from said surface of said middle panel when said proximal end panel has been moved to said overlap position;
   d) means for locking said proximal end panel in said overlap position; and,
   e) means for locking said distal end panel in said overlap position, said distal end panel locking means including a tab located on said middle panel for engaging an edge of the distal end panel when said distal end panel is moved to said overlap position.

* * * * *